United States Patent
Shelley et al.

(10) Patent No.: US 7,919,753 B2
(45) Date of Patent: Apr. 5, 2011

(54) METHOD FOR PERFORMING IR SPECTROSCOPY MEASUREMENTS TO QUANTIFY A LEVEL OF UV EFFECT

(75) Inventors: Paul H. Shelley, Lakewood, WA (US); Greg J. Werner, Puyallup, WA (US); Diane R. LaRiviere, Seattle, WA (US); Gwen M. Gross, Redmond, WA (US)

(73) Assignee: The Boeing Company, Chicago, IL (US)

( * ) Notice: Subject to any disclaimer, the term of this patent is extended or adjusted under 35 U.S.C. 154(b) by 101 days.

(21) Appl. No.: 12/164,026

(22) Filed: Jun. 28, 2008

(65) Prior Publication Data

US 2009/0321647 A1  Dec. 31, 2009

(51) Int. Cl.
*G01L 1/24* (2006.01)
*G01N 21/00* (2006.01)
*G01N 21/25* (2006.01)

(52) U.S. Cl. ......... 250/339.11; 250/339.09; 250/339.07; 356/303; 356/306

(58) Field of Classification Search ............. 250/339.07, 250/339.09, 339.11; 356/302, 303, 306, 356/326, 939
See application file for complete search history.

(56) References Cited

U.S. PATENT DOCUMENTS

| | | | | |
|---|---|---|---|---|
| 6,495,833 B1 * | 12/2002 | Alfano et al. | ............... | 250/341.8 |
| 2002/0109093 A1 * | 8/2002 | Kelley | ..................... | 250/339.09 |
| 2002/0113212 A1 * | 8/2002 | Meglen et al. | ........... | 250/339.05 |
| 2004/0155190 A1 * | 8/2004 | Shelley et al. | ........... | 250/339.11 |
| 2004/0159789 A1 * | 8/2004 | Treado et al. | ............ | 250/339.07 |

OTHER PUBLICATIONS

Hamid, S. H. (2000), Ultraviolet-induced degradation of Ziegler-Natta and metallocene catalyzed polyethylenes. Journal of Applied Polymer Science, 78: 1591-1596. doi: 10.1002/1097-4628(20001128)78:9<1591::AID-APP30>3.0.CO;2-A.*

Amin, M. B., Hamid, S. H. and Rahman, F. (1995), Prediction of mechanical properties of weather-induced degraded plastics in saudi arabia. Journal of Applied Polymer Science, 56: 279-284. doi: 10.1002/app.1995.070560219.*

* cited by examiner

*Primary Examiner* — David P Porta
*Assistant Examiner* — Jessica L Eley
(74) *Attorney, Agent, or Firm* — Tung & Associates

(57) ABSTRACT

A method of non-destructively determining the amount of ultraviolet degradation of a surface and/or paint adhesion characteristics of the surface corresponding with UV damage including determining a physical property of a composite material/surfacing film by providing a series of composite materials/surfacing films which are subjected to increasing UV light exposure to create a set of UV damage standards, collecting mid-IR spectra on those standards, performing data pre-processing and then multivariate calibration on the spectra of the composite materials/surfacing films, and using that calibration to predict the UV damage for samples in question.

20 Claims, 3 Drawing Sheets

METHOD FOR PERFORMING IR SPECTROSCOPY MEASUREMENTS TO QUANTIFY A LEVEL OF UV EFFECT

CROSS REFERENCE TO RELATED APPLICATIONS

This application is related to co-pending U.S. patent application Ser. Nos. 12/164,023, and 12/164,025; and 12/164,022; and 12/164,017, all filed concurrently herewith on Jun. 28, 2008, each of which applications is incorporated by reference herein in its entirety.

FIELD OF THE INVENTION

This invention generally relates to Infrared (IR) measurement methods and apparatus, and more particularly provides a method for performing non-destructive IR spectroscopy measurements of surface characteristics of materials including quantifying a level of ultraviolet (UV) exposure damage to an organic material containing surface, such as a surface of a polymer composite material, including polymer composite materials used in aircraft.

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety of organic as well as inorganic materials.

For example, organic polymer materials including resin-fiber composite materials may degrade over time due to a variety of reasons including ultraviolet (UV) light exposure. Chemical degradation to a polymer structure may occur, thereby affecting the desired properties of the polymer structure including structural integrity such as strength of a composite material or adhesion of an organic surface coating on said composite material.

Chemical degradation of a polymer material may be caused by exposure to normal environmental sources of UV such as sunlight as well as exposure to artificial sources of UV such as metal halide light sources and other indoor light sources. Exposure of organic materials to UV radiation may result in the breaking of existing polymer chemical bonds and/or the formation of new polymer chemical bonds. Maintenance of organic containing materials subjected to UV light exposure requires a determination of the degree of UV-induced physical and/or chemical degradation of the organic containing material, including polymer composite materials or coatings thereon.

For example, polymer composite materials such as fiber-resin materials including carbon reinforced fiber have been used as structural materials, for example in portions of an aircraft. Preparation and use of such polymer composite materials may further include the use of surface treating polymers such as epoxies. The exposure of polymer composite materials to UV energy may result in the degradation of desirable properties of such materials including strength and adhesion properties to other materials, such as overlying coatings of material, including paint. Although the exposure to such material to UV light may result in visual indications of UV damages including gradations of discoloration, such visual indications of damaged or compromised composite material are subjective and not sufficiently reliable or quantifiable to assess a degree of degradation and a level of required maintenance. For example, UV exposure is mitigated or repaired with hand wiping using an 80% acetone and 20% water solution until the surface damage is removed. To the Inventor's knowledge, no adequate non-destructive method exists in the prior art to determine when the mitigation is sufficient or if more mitigation is needed to insure good paint adhesion to a repaired surface.

One non-destructive method of ascertaining the condition of a polymer composite material, such as the degree of heat damage to composite materials includes IR spectroscopy of the composite material as outlined in U.S. Pat. No. 7,115,869, which is hereby incorporated by reference in its entirety.

Other non-destructive methods in the prior art include using IR spectroscopy to determine the amount of a chromated conversion coating on a metallic substrate (U.S. Pat. No. 6,794,651), determining the amount of an anodize coating on a metallic substrate, (U.S. Pat. No. 6,784,431), determining an amount of opaque coating on a substrate (U.S. Pat. No. 6,903,339), and determining an amount of heat exposure to a resin-fiber composite substrate (U.S. Pat. No. 7,115,869), all of which are fully incorporated by reference herein.

None of the above methods and associated devices, however, disclose a method or device that is suitable for performing IR spectroscopy to quantify a level of UV energy induced damage to an organic material containing surface, and to thereby determine a degree of damage present in the organic material containing surface, particularly in a field environment, such as in aircraft maintenance.

Thus, there is a continuing need for improved IR non-destructive testing methods including a method that is suitable for performing IR spectroscopy to quantify a level of UV energy induced damage in organic material containing surface, such as a surface of a polymer composite material, and to thereby determine a degree of damage present in the organic material containing surface, particularly in a field environment, such as in aircraft manufacture and maintenance.

Therefore it is an object of the invention to provide a method that is suitable for performing IR spectroscopy to quantify a level of UV energy induced damage in an organic material containing surface, such as a surface of a polymer composite material, and to thereby determine a degree of damage present in the organic material containing surface, particularly in a field environment, such as in aircraft manufacture and maintenance.

SUMMARY OF THE INVENTION

A method of non-destructively determining the amount of ultraviolet degradation of a surface and/or paint adhesion characteristics of the surface corresponding with UV damage including determining a physical property of a composite material/surfacing film by providing a series of composite materials/surfacing films which are subjected to increasing UV light exposure to create a set of UV damage standards, collecting mid-IR spectra on those standards, performing data pre-processing and then multivariate calibration on the spectra of the composite materials/surfacing films, and using that calibration to predict the UV damage for samples in question.

In one embodiment a method of non-destructively determining the amount of ultraviolet degradation of a surface is provided, the method including irradiating a surface with infrared energy over a spectrum of wavelengths; detecting said infrared energy reflected from said surface over said spectrum of wavelengths; performing multivariate analysis on the spectrum of said reflected infrared energy; comparing results of said multivariate analysis with a predetermined calibration between model infrared energy spectra including said spectrum of wavelengths collected from a plurality of model material surfaces, said plurality of model material surfaces each including a known level of said ultraviolet degradation of said model material; and, determining said amount of said ultraviolet degradation of said surface based on said predetermined calibration.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing a method of non-destructively determining the physical property of a material surface where the method may be accomplished by making an infrared (IR) spectroscopy measurement with an IR spectrometer, preferably a portable FT-IR spectrometer, and performing a multivariate calibration and prediction to determine a level of ultraviolet (UV) energy induced damage present in organic material containing surfaces including polymer composite material surfaces and/or organic containing material on the polymer composite material surfaces, including as part of an aircraft maintenance process.

It will be appreciated that although the invention is particularly explained with reference to using IR spectroscopy to determine a level of UV exposure damage to composite material surfaces used in portions of aircraft, that the invention may additionally be advantageously used to quantify a level UV exposure damage to organic containing material surfaces in general.

While either a portable or non-portable IR spectrometer may be used to carry out the IR spectroscopy measurements according to the present invention, and the spectrum of wavelengths used to make the IR spectroscopy measurements may include all or a portion of the wavelengths between about 2500 and about 15000 nanometers (2.5 to 16.7 microns or 4000 to 600 wavenumbers ($cm^{-1}$)). In a preferred embodiment, a hand-held portable spectrometer capable of performing Fourier transform infrared (FT-IR) spectroscopy measurements is used to perform the IR spectroscopy measurements according to the present invention.

The hand-held portable FT-IR spectrometer preferably has the capability to supply source IR energy to a sample at a predetermined incident angle between about 30 to about 60 degrees, most preferably 45 degrees, and collect reflected light from the sample through a broad range of angles including the incident angle. The hand-held portable FT-IR device preferably has the ability to make specular-diffuse reflectance IR spectroscopic measurements.

Figure 1:
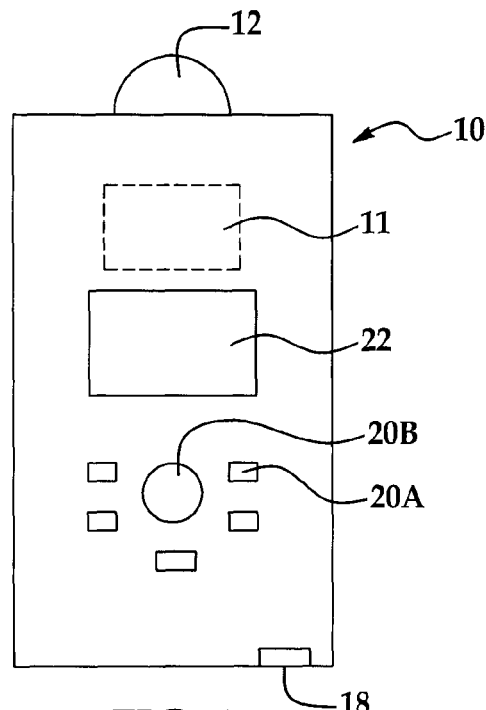
FIG. 1 is a schematic diagram of an exemplary hand-held portable IR spectrometer suitably used to make IR spectroscopy measurements according to an embodiment of the invention.

Referring to FIG. 1 is shown a top view of a portable (handheld) IR spectrometer 10 according to an embodiment of the invention. The portable IR spectrometer 10 may have the capability of performing either FT-IR or near infrared IR spectroscopy measurements, but in a preferred embodiment at least has the capability of performing FT-IR spectroscopy measurements. By the term hand-held portable is meant an instrument that may be easily carried and picked up and move about to make IR spectroscopy measurements by an average person, e.g., has a weight of less than about 8 pounds and a size of less than about 1 ft by 1 ft.

In some embodiments, the portable FT-IR spectrometer 10 shown in FIG. 1 is capable of performing FT-IR spectroscopy measurements over a wavelength range of about 2.5 to 16.7 microns or 4000 to 600 wavenumbers ($cm^{-1}$).

The portable IR spectrometer 10 also preferably includes a computer processor and memory (e.g., 11) and may be interfaced (placed in communicated with) with other computing devices (e.g., USB port 18). The portable IR spectrometer 10 may be supplied power by one or more batteries. The portable IR spectrometer 10 is preferably programmable and/or capable of accepting, storing, and executing preprogrammed instructions for carrying out FT-IR spectroscopy measurements. The portable IR spectrometer 10 preferably has the capability to provide incident IR light (energy) and collect reflected IR spectra (e.g., through one or more IR transparent energy windows/domes e.g., 12) over a range of an operating wavelength range (e.g., 2.5 to 16.7 microns). For example the incident IR energy may be provided at various incident angles to a sample and collected over a broad range of wavelengths including an incident angle. The portable IR spectrometer 10 preferably has the ability to store collected IR spectra and perform mathematical manipulation of the data comprising the spectra including multivariate analysis of the spectra. The portable IR spectrometer 10 may include interactive buttons e.g., 20A, 20B, and/or softkeys on an interactive LCD or LED touchscreen 22. It will be appreciated that the portable IR spectrometer 10 may be of any suitable ergonomic shape to enhance the portability and ease of holding and manipulating the spectrometer to carryout field IR spectroscopy measurements.

In addition, suitable calibration background reference standard materials and wavelength reference standard materials may be provided for calibrating the IR spectrometer prior to performing IR spectroscopy measurements according to embodiments of the invention.

In one embodiment, an IR spectrometer used to carry out an IR spectroscopy measurement according to the present invention, such as the portable IR spectrometer 10, may be provided and have stored in memory one or more multivariate calibrations that are made for the composite materials and composite surface layers similar to the materials in question to be measured. The reference IR spectral standards used in each multivariate calibration are with respect to material in a similar condition to an area of the sample with a known level (e.g. baseline), of UV induced damage including an absence of the UV induced damage.

In addition, a previously determined multivariate calibration of a plurality of model IR spectra with a plurality of model samples each having known levels of the UV induced damage (as exemplified by carefully measured and controlled UV exposure) may be stored in memory within the IR spectrometer to thereby calibrate the IR spectrometer such that an in-situ analysis of measured IR spectra taken from an actual sample may be performed to determine a level of the UV damage according to the multivariate calibration. Preferably, a quantified (numerical) level of the UV exposure may be determined by the in-situ analysis (e.g., in kilojoules per meter squared ($Kj/m^2$)) and stored or output by IR spectrometer used to make the measurement, such as the IR spectrometer 10, or a pass/fail type determination (level of damage is above or below a threshold numerical value) and resulting indication thereof may stored or output.

For example, a separately measured physical property corresponding to levels of UV damage to a polymer composite material surface (and/or organic containing coating on the surface) may include any measurable and/or chemical property of the composite material surface that is altered by UV damages including properties such as paint adhesion results, for example, the results of a standard scribe adhesion test or other industry standard paint adhesion test, as are known in the art.

The portable IR spectrometer 10, or another IR spectrometer used to carry out IR spectroscopy measurements according to embodiments of the invention, preferably includes a computer processor capable of multivariate analysis of the IR spectra. For example, the IR spectrometer (or an associated controller) preferably has the ability to mathematically and statistically correlate and determine changes in a plurality of variables (e.g., IR spectra including reflectance at a plurality of wavelengths) with respect to one or more reference IR spectra. In addition, multivariate statistical approaches may be used to correlate the statistically determined changes in the plurality of variables (e.g., FT-IR determined absorbance and/or reflectance at one or more wavelengths) with one or more second variables or (e.g. a change in a separately measured material property (chemical and/or physical change) that is correlated by multivariate analysis to relative changes in the IR spectra).

There are many suitable multivariate calibration techniques that may be used with IR spectral data according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are several data processing methods that may be suitably used in connection with suitable multivariate statistical approaches including smoothing, normalization, taking first and second derivatives of the IR spectra, and peak enhancement methods.

In addition, multivariate calibration of collected IR spectra may include the selection and clustering together of groups of wavelengths on which to perform a regression analysis to determine a corresponding change in the IR spectra (spectrum) (e.g., reflectance) with respect to reference spectra (spectrum). It will be appreciated that an individual IR spectrum may be formed from several IR spectra (e.g., by averaging techniques known in the art). In addition, the raw IR spectra may transformed into second IR spectra by taking first and/or second derivatives and performing smoothing and/or peak enhancement as well as carrying out regression analysis. For example, manipulation the raw IR spectra by smoothing algorithms prior to or following taking a first derivative and then quantifying a degree of change of the IR spectra from a reference spectrum (similarly processed) according to a regression or partial lest squares analysis may be performed.

In addition, the IR spectroscopy measurement process may include collecting reference IR spectra (including calculated absorbance and/or reflectance) which may serve as a baseline from which to determine relative changes in sample IR spectra by multivariate calibration. In addition, various processing methods as are known in the art may be used to form a single IR spectrum from a collection of a plurality of collected IR spectra, including various averaging techniques, for example to improve a signal to noise ratio, prior to carrying out multivariate analysis to determine a change from reference spectrum. It will be appreciated that the change may include a change at one or more wavelengths including clusters of wavelengths.

Figure 2:
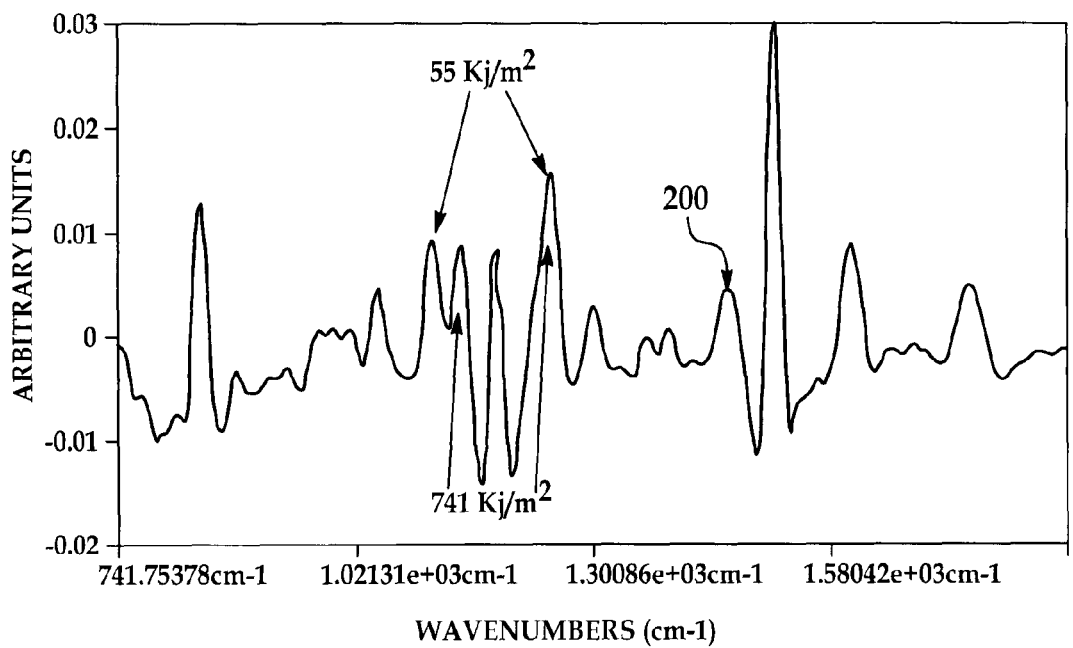
FIG. 2 are exemplary mid-IR spectra as they change with increasing UV exposure. Shown are first derivative spectra with 7 smoothing points to highlight the changes with UV exposure.

Referring to FIG. 2 are shown IR spectra 200 (e.g., four superimposed spectra) following transformation by taking a first derivative and employing a smoothing algorithm with 7 smoothing points. The spectra show a progressive change with UV exposure on the IR spectral standards (model samples) used to make the spectra. Multivariate calibration is then used such as regression or partial least squares to determine a calibration model that can be used to predict UV damaged samples in question (actual samples).

Figure 3:
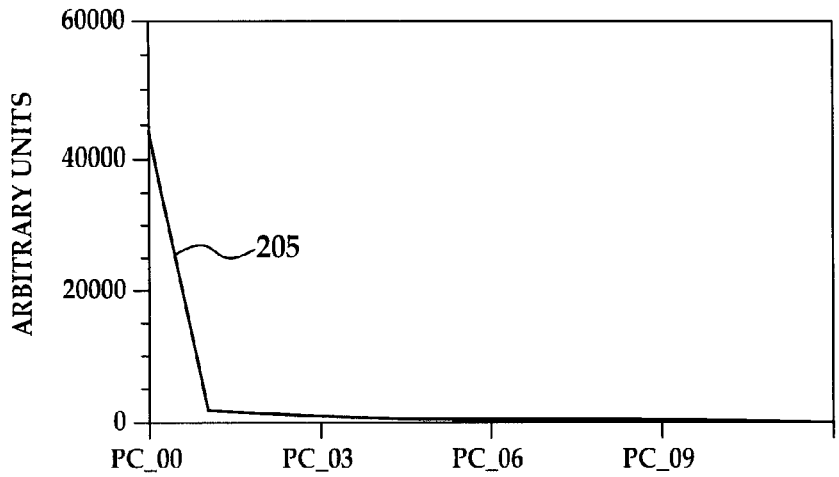
FIG. 3 shows a typical multivariate calibration model used for UV damage measurement on a composite surface that has an epoxy surfacer material on it.

Referring to FIG. 3 is shown an exemplary multivariate calibration model made from IR spectra taken from model samples with carefully controlled UV exposure. The calibration model as shown in FIG. 3 includes four blocks A, B, C, D to show the quality of the model. For example, the regression coefficients 204 (upper right block B) are used for prediction of UV exposure on UV damaged samples in question. In an exemplary approach, a dot product of the new spectrum of a damaged sample in question (after the same derivative and smoothing pre-processing is performed on the new spectrum in question) is taken with the regression coefficients vector 204 which gives a number that corresponds to UV exposure of the sample in question as shown in block D.

Referring to upper left block A, are shown individual sample "scores" e.g., 202A, 202B to show distribution of sample data. Lower left block C shows residual variance 205 to show that all useful data is captured in the model while lower right block D is predicted (vertical axis) versus measured (horizontal axis) UV exposure from a model validation regression function 206 according to individual measurements (207A, 207B and 207B) e.g., 207B left out as a leave-one-out cross validation.

It will be appreciated that the model IR spectral standards (model samples) with carefully controlled ultraviolet damage that are used in determining the amount of UV damage in a measured sample may further include a calibration that corresponds to adhesion properties, e.g., determined from paint adhesion data determined from adhesion tests performed on the spectral standards. Therefore, it will be appreciated that the different levels of UV damage present in model IR spectral standards and corresponding IR spectra used to establish a predetermined calibration model between changes in model IR spectra and the level of UV damage may include a correlation to similar UV damage as reflected by paint adhesion data. Thus, the level of UV damage in some embodiments may correspond to paint adhesion as determined on an equivalently damaged organic material containing surface. It is noted that it has been found in some embodiments that since paint adhesion is the only property affected by UV damage, calibration to UV exposure is preferred compared to calibration to paint adhesion since it is easier and just as effective.

It will also be appreciated that a composite material surface e.g., polymer fiber-resin composite material such as carbon fiber reinforced polymer, may include an organic surface finishing product, such as an epoxy. Thus, it will be appreciated that reference herein to a polymer composite material may include the presence of a coating of an organic material containing surface.

For example, by analyzing the data according to multivariate calibration (processing IR spectra collected from carefully controlled UV spectral standards with a multivariate calibration routine) a model may be generated by the multivariate calibration and used to predict the UV exposure and/or paint adhesion characteristics of samples in question (measured samples), e.g., after performing the same pre-processing for the calibration IR spectra and for the IR spectra of the samples in question.

It will be appreciated that the UV damage may be on organic material containing coatings on the polymer composite material surface or on a surface of the polymer composite material itself. It will also be appreciated that an IR spectroscopy measurement process may include taking IR spectra at several locations from the top to the bottom of an airplane fuselage since the UV lighting source is probably above the airplane and the UV damage is probably minimal on the under side of the fuselage. In addition, when making the IR spectroscopy measurement, it may be preferable, depending on if the UV damage is in the composite material itself, that the incident IR energy be provided at an orientation perpendicular to a composite fiber direction e.g., in composite fiber-resin material, such as carbon fiber reinforced polymer (or plastic) (CFRP).

Figure 4:
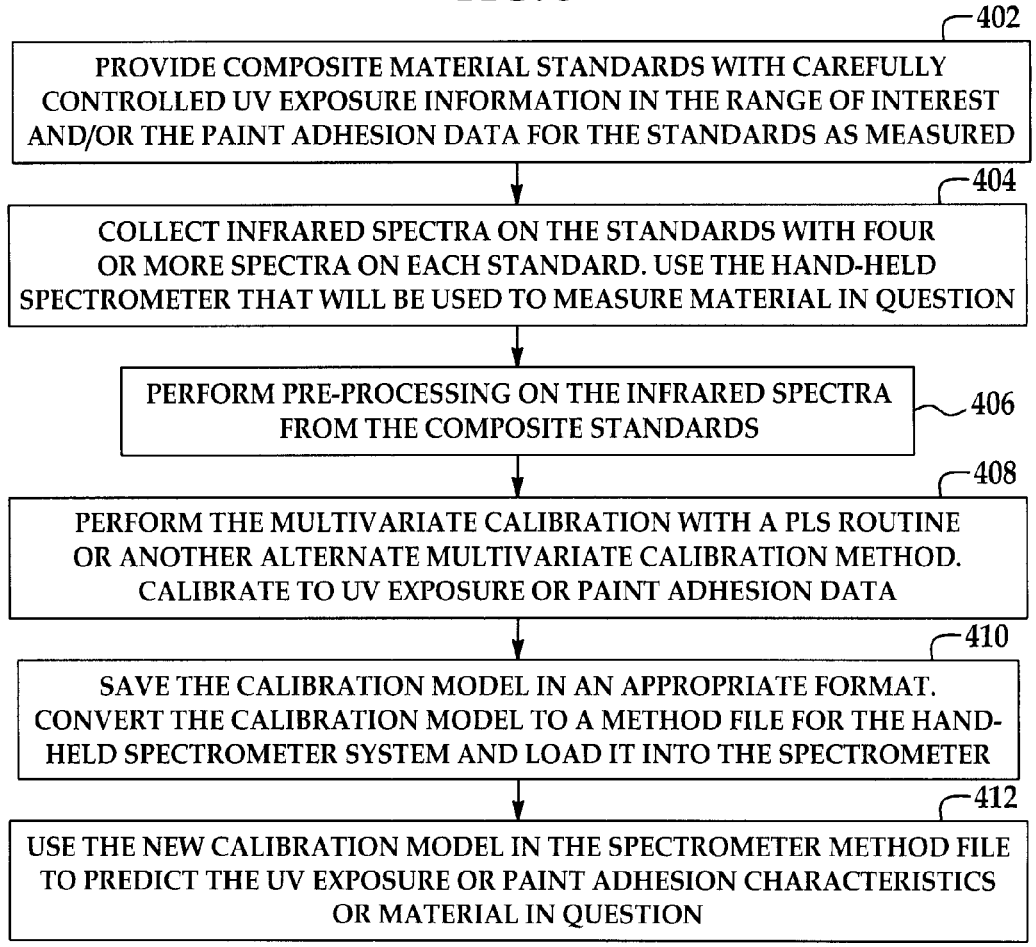
FIG. 4 is an exemplary IR spectroscopy measurement process flow diagram to map a UV affected polymer composite material surface according to an embodiment of the invention.

Referring to FIG. 4 is shown an exemplary IR spectroscopy measurement process according to the present invention including a method of multivariate calibration for thermal damage with mid-IR spectra. As shown in block 402 of flow diagram 400 in FIG. 4, the UV damage calibration begins with CFRP standards that are carefully UV exposed and then tested to obtain paint adhesion properties. Block 404 shows the mid-IR spectral data collection step and the pre-processed infrared spectra are shown in FIG. 2. Block 406 shows the data pre-processing step. Block 408 shows the multivariate calibration step and FIG. 3 shows the multivariate regression (block D) including the regression coefficients (block B) that result from that calibration. Block 410 shows the step where the multivariate calibration is saved in an appropriate format and then loaded into the hand-held mid-IR device that will be used to read UV damage on CFRP material in question. Block 412 shows material in question being predicted for paint adhesion characteristic values that would indicate the extent of UV damage in the material in question.

As will be appreciated, if the original standards are predicted, one can develop an accuracy figure based on the difference between the known physical property e.g., stress numbers resulting from the paint adhesion results and those predicted by the multivariate calibration method according to the invention.

Figure 5:
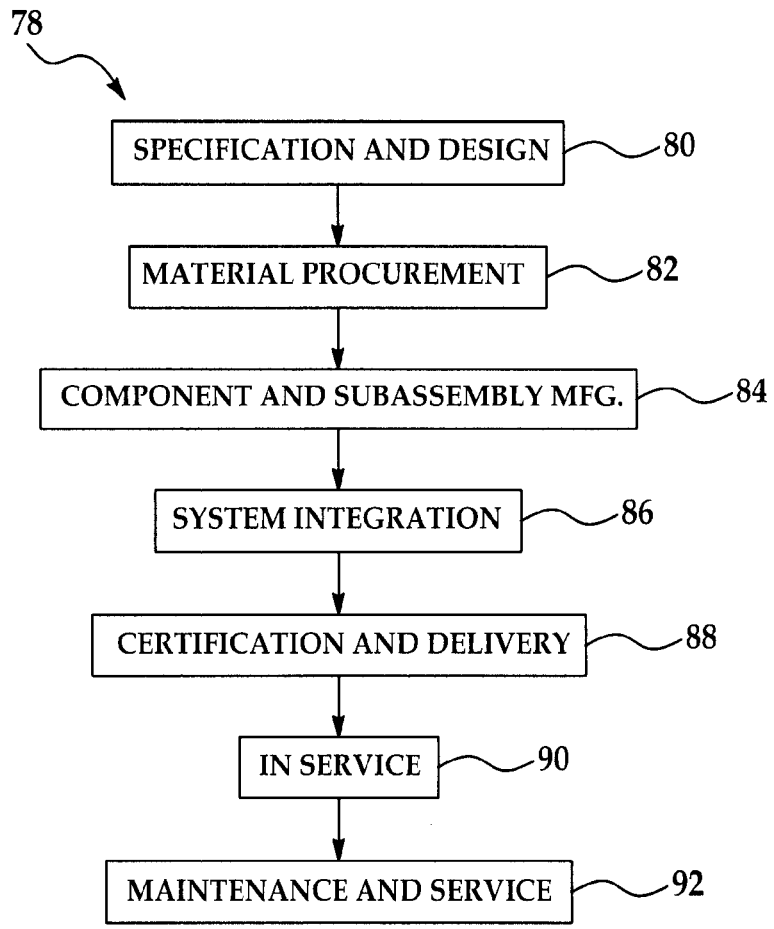
FIG. 5 is a flow diagram of an aircraft and service methodology according to an embodiment of the invention.
Figure 6:
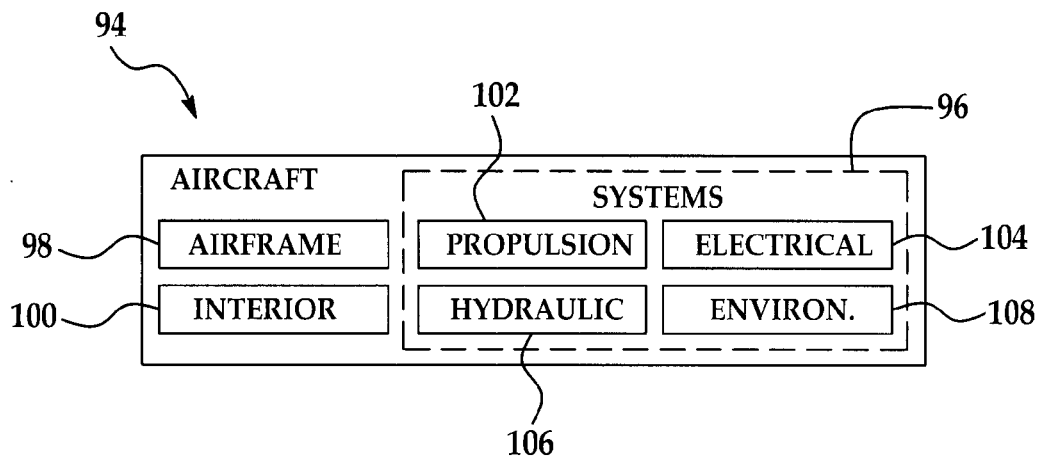
FIG. 6 is a block diagram of an aircraft according to an embodiment of the invention.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of non-destructively determining by infrared spectroscopy the amount of ultraviolet degradation of an organic polymer containing surface comprising:

irradiating said organic polymer containing surface with infrared energy comprising a spectrum of wavelengths;

detecting and collecting at least one spectrum of said infrared energy reflected from said surface comprising said spectrum of wavelengths;

performing multivariate analysis on the at least one spectrum of said reflected infrared energy;

comparing results of said multivariate analysis with a predetermined calibration between model infrared energy spectra comprising said spectrum of wavelengths collected from a plurality of model organic polymer containing surfaces, said plurality of model organic polymer containing surfaces each comprising a known amount of said ultraviolet degradation including a known amount of ultraviolet exposure; and, determining said amount of said ultraviolet degradation of said organic polymer containing surface based on said predetermined calibration.

2. The method of claim 1, wherein said multivariate analysis comprises multivariate statistical approaches to determine changes in absorbance and/or reflectance values at selected groups of wavelengths comprising said spectrum of wavelengths, said changes with respect to a reference spectrum.

3. The method of claim 1, wherein said surface comprises a polymer composite material.

4. The method of claim 1, wherein said ultraviolet degradation is correlated with a separately measured amount of UV exposure or a physical property of said surface.

5. The method of claim 4, wherein said separately measured physical property of said surface comprises adhesion of paint to said surface.

6. The method of claim 1, wherein said spectrum of wavelengths is from about 2500 and about 15000 nanometers.

7. The method of claim 1, wherein said steps are performed by a hand-held portable IR spectrometer.

8. The method of claim 1, wherein said hand-held portable IR spectrometer is a Fourier transform (FT-IR) spectrometer.

9. The method of claim 1, wherein said steps comprise an aircraft maintenance process performed on an aircraft.

10. The method of claim 1, wherein said predetermined calibration comprises a regression analysis of said model infrared spectra with respect to said known amount of ultraviolet degradation.

11. The method of claim 1, wherein said predetermined calibration comprises creating said plurality of model material surfaces, each with a different amount of said known amount of ultraviolet degradation.

12. A method of non-destructively determining by infrared spectroscopy the amount of ultraviolet degradation of an organic polymer containing surface comprising:
   irradiating said organic polymer containing surface with infrared energy comprising a spectrum of wavelengths;
   detecting and collecting at least one spectrum of said infrared energy reflected from said organic polymer containing surface comprising said spectrum of wavelengths;
   performing multivariate analysis on the at least one spectrum of said reflected infrared energy;
   comparing results of said multivariate analysis with a predetermined correlation between model infrared energy spectra comprising said spectrum of wavelengths collected from a plurality of model organic polymer containing surfaces, said plurality of model polymer organic containing surfaces each comprising a known amount of said ultraviolet degradation including a known amount of ultraviolet exposure; and,
   determining said amount of said ultraviolet degradation of said organic polymer containing surface based on said predetermined correlation, wherein said ultraviolet degradation is correlated with a separately measured amount of UV exposure and/or a physical property of said organic polymer containing surface.

13. The method of claim 12, wherein said multivariate analysis comprises multivariate statistical approaches to determine changes in absorbance and/or reflectance values at selected groups of wavelengths comprising said spectrum of wavelengths, said changes with respect to a reference spectrum.

14. The method of claim 12, wherein said organic polymer containing surface comprises a polymer composite material.

15. The method of claim 12, wherein said separately measured physical property of said surface comprises adhesion of paint to said surface.

16. The method of claim 12, wherein said predetermined calibration comprises performing a regression analysis of said model infrared energy spectra with respect to said known level of ultraviolet degradation.

17. The method of claim 12, wherein predetermined calibration comprises creating said plurality of model organic polymer containing surfaces, each with a different amount of said known amount of ultraviolet degradation.

18. The method of claim 12, wherein said steps are performed by a hand-held portable IR spectrometer.

19. The method of claim 18, wherein said steps comprise an aircraft maintenance process performed on an aircraft.

20. A method of non-destructively determining by infrared spectroscopy the amount of ultraviolet degradation of an organic polymer containing surface on an aircraft comprising:
   collecting model reflected infrared energy spectra comprising a spectrum of wavelengths from a plurality of model organic containing surfaces, said plurality of model organic polymer containing surfaces each comprising a known amount of said ultraviolet degradation including a known amount of ultraviolet exposure;
   performing multivariate analysis of said model infrared energy spectra including performing a regression analysis to determine a calibration between said model infrared energy spectra and said known amount of said ultraviolet degradation including a known amount of ultraviolet exposure;
   irradiating said organic polymer containing surface with infrared energy comprising said spectrum of wavelengths;
   detecting and collecting at least one spectrum of said infrared energy reflected from said organic polymer containing surface comprising said spectrum of wavelengths;
   performing multivariate analysis on the at least one spectrum of said reflected infrared energy;
   comparing results of said multivariate analysis with said calibration; and,
   determining said amount of said ultraviolet degradation of said organic polymer containing surface based on said calibration.

* * * * *